United States Patent [19]

Isa et al.

[11] 3,974,194

[45] Aug. 10, 1976

[54] METHOD OF SEPARATING COBALT CATALYST FROM A LIQUID POLYOL ESTER PRODUCT

[75] Inventors: Hiroshi Isa, Funabashi; Takeo Inagaki, Yachiyo; Yasuhiro Kiyonaga, Musashino; Masuzo Nagayama, Tokyo, all of Japan

[73] Assignee: Lion Fat & Oil Co., Ltd., Tokyo, Japan

[22] Filed: Sept. 30, 1974

[21] Appl. No.: 510,590

[30] Foreign Application Priority Data
Oct. 6, 1973  Japan.............................. 48-112721

[52] U.S. Cl............................. 260/410.6; 260/497 C
[51] Int. Cl.².......................................... C09F 5/08
[58] Field of Search................ 260/410.6, 410.9 R, 260/533 A, 497 C, 428

[56] References Cited
UNITED STATES PATENTS

| 2,739,169 | 3/1956 | Hagemeyer | 260/497 C |
|---|---|---|---|
| 2,868,813 | 1/1959 | Heisler | 260/410.9 R |
| 2,911,422 | 11/1959 | Ersoli | 260/533 A |
| 3,507,891 | 4/1970 | Hearne | 260/410.9 R |
| 3,819,727 | 6/1974 | Ferrari | 260/497 C |
| 3,856,832 | 12/1974 | Keblys | 260/410.9 R |

FOREIGN PATENTS OR APPLICATIONS

| 850,675 | 9/1970 | Canada | 260/410.9 R |
|---|---|---|---|

*Primary Examiner*—Patrick P. Garvin
*Assistant Examiner*—John F. Niebling
*Attorney, Agent, or Firm*—Woodhams, Blanchard and Flynn

[57] ABSTRACT

In the method of manufacturing liquid polyol esters of carboxylic acid by making an olefin having 3 or more carbon atoms, carbon monoxide and polyhydric alcohol react with one another in the presence of a cobalt compound catalyst, the steps comprising heating the thus reacted mixture to distill out unreacted olefin and so forth, thereafter cooling the distillation residue and separating it into the ester of polyhydric alcohol and the cobalt compound.

14 Claims, No Drawings

METHOD OF SEPARATING COBALT CATALYST FROM A LIQUID POLYOL ESTER PRODUCT

BACKGROUND OF THE INVENTION a. Field of the Invention

The present invention relates to a method of separating the catalyst from the reaction mixture obtained at the time of manufacturing liquid polyol esters of carboxylic acid by reacting olefin, carbon monoxide and polyhydric alcohol in the presence of a catalyst consisting of a cobalt compound.

b. Description of the Prior Art

Esters of polyhydric alcohols having a wide range of use as lubricants, plasticizers, cosmetic materials, surface active agents, etc. have hitherto been manufactured by effecting reaction between natural fatty acids and polyhydric alcohols. However, the natural fatty acids are biased in respect of the distribution of carbon atoms and the resources of natural fatty acids having 6 to 10 carbon atoms as required for materials for use in lubricants for aircraft or heatresisting plasticizers are quite limited. Under such circumstances, with an increase of uses in these fields, the art of esterification by the use of synthetic fatty acids has come into the limelight from the viewpoint of stable supply thereof.

As the method of manufacturing synthetic fatty acids, there are known the Reppe method and Koch method utilizing olefins as the starting material and also the paraffin oxidation method utilizing paraffin as the starting material, but both methods are attended with the forming of side-chain fatty acids as byproducts. These side-chain fatty acids are remarkably inferior to the straight-chain fatty acids in reactivity, so that they necessitate a considerably complicated process for completion of the esterification reaction with polyhydric alcohol, and accordingly, it is difficult to manufacture esters of polyhydric alcohol directly from such fatty acids.

Meanwhile, there have also been made various attempts to synthesize esters directly by the use of olefin constituting the starting material for synthetic fatty acids, carbon monoxide and alcohol with a view to further simplifying the manufacturing method, but these attempts have so far been confined to esterifications with lower monohydric alcohols, such as methanol and ethanol, and direct synthesis of industrially useful esters with polyhydric alcohols is unprecedented.

On the other hand, in the case of the method utilizing the so-called oxo reaction wherein an aldehyde is manufactured by making olefin, carbon monoxide and hydrogen react with one another in the presence of a cobalt compound catalyst, said catalyst assumes the form of dicobalt octacarbonyl or cobalt carbonyl hydride or derivative thereof at the end of the reaction, and accordingly, if the reaction product is directly subjected to distillation, said cobalt compound will be fractionated and the resulting product will be colored, or said cobalt compound will decompose within the still column, giving rise to cobalt metal and hampering smooth operation. Therefore, there is used either the process comprising treating said cobalt compound with hydrogen or steam at a high temperature to convert it into cobalt metal and thereafter transforming this cobalt metal to a form usable for the reaction, or the process comprising treating said cobalt compound with an aqueous solution of acetic acid to convert it into cobalt acetate and thereafter transforming this cobalt acetate to a form usable for the reaction. Admitting that both processes are also applicable in the case of making olefin, carbon monoxide and alcohol react with one another, yet they are industrially undesirable on account of the complicated process involved therein.

SUMMARY OF THE INVENTION

The object of the present invention is to provide a method of manufacturing liquid polyhydric alcohol carboxylic esters by making olefin having 3 or more carbon atoms, carbon monoxide and polyhydric alcohol react with one another in the presence of a cobalt compound catalyst, which method renders it possible to recover said catalyst in a form suitable for reuse thereof without resorting to any complicated means and comprises the steps of heating the reaction mixture obtained through said reaction to thereby distill the unreacted olefin and so forth therefrom and cooling it thereafter.

DESCRIPTION OF THE PREFERRED EMBODIMENTS

According to the method of the present invention, olefin having 3 or more carbon atoms, carbon monoxide and polyhydric alcohol are made to react with one another in the presence of a cobalt compound catalyst, together with pyridine base as occasion demands, by heating and increasing pressure, the resulting reaction mixture is heated, preferably in the presence of carboxylic acid, to distill out unreacted olefin and pyridine base and is cooled thereafter, whereby the distillation residue can be separated into liquid polyhydric alcohol ester and solid or paste-like cobalt compound.

The foregoing starting material olefin is an α- or inner-olefin having 3 to 20 carbon atoms, and it can have side chains; it includes, for instance, propylene, butene-1, hexene-1, 2-ethyl hexene-1, octene-1, hexene-2, octene-2, tetradecene-3 as well as their analogues, and mixtures thereof are effective as well.

As the starting material polyhydric alcohol, any polyhydric alcohol, such as ethylene glycol, trimethylol propane, pentaerythritol and their analogues, is effective. The ratio of said olefin to said polyhydric alcohol to be employed can be changed at will according to the esterification efficiency of the polyhydric alcohol applied, but in order to esterify the entirety of the hydroxyl groups, it is desirable to make the amount of olefin a stoichiometric excess.

As the starting material carbon monoxide, it is allowed to contain a modicum of hydrogen as an impurity, but the presence of more than 10% by volume of hydrogen therein will entail an increase of the impurities within the product ester and is therefore undesirable.

As the cobalt compound to act as catalyst, dicobalt octacarbonyl or compounds capable of forming dicobalt octacarbonyl, cobalt carbonyl hydride or derivative thereof under the reaction conditions are effective. As such compounds, there are cobalt octanoate, cobalt stearate, cobalt hydroxide and their analogues. The appropriate amount of said cobalt compound to be applied is in the range of 0.001 to 0.1 mole relative to 1 equivalent of hydroxyl group of said polyhydric alcohol in terms of cobalt metal.

As the applicable pyridine base, there are pyridine, β-picoline, γ-picoline, 3,5-lutidine, 4-ethyl pyridine and their analogues, and the appropriate amount of said pyridine base is in the range of 1 to 100 moles, preferably 3 to 50 moles, relative to 1 mole of the catalyst metal.

The appropriate temperature for the reaction is more than 90°C, and, in view of the fact that the catalyst decomposes when said temperature is more than 250°C, it is desirable to be in the range of 90° to 250°C. The pressure for reaction is desirable to be more than 5 Kg/cm$^2$, preferably more than 90 Kg/cm$^2$, but elevation of said pressure in excess of 300 Kg/cm$^2$ will be without value. Further, by making water present in the reaction zone, the reaction can be accelerated and also the rate of recovery of the catalyst can be raised.

In the hydroesterified mixture thus obtained, there is contained the cobalt compound catalyst, dissolved therein in the form of a cobalt carbonyl derivative. Mere heating of this reaction mixture cannot separate said catalyst from it, but through the process of distilling out the unreacted olefin and/or pyridine base and thereafter cooling the reaction mixture, the catalyst becomes a salt which is scarcely soluble in the polyhydric alcohol ester and it can be easily separated from the ester by a filtration or centrifugal separation process. In this connection, in the case where water is not present in the reaction zone, it is desirable to make carboxylic acid present therein at the time of distillation by heating. As the carboxylic acid for this purpose, fatty acids having 2 to 21 carbon atoms, such as butyric acid, caprylic acid, palmitic acid, etc., are effective. Also, it is possible to apply aromatic carboxylic acids having 7 to 9 carbon atoms such as benzoic acid, but these acids may be esterified when the separated and recovered catalyst is reused, and therefore, a fatty acid whose number of carbon atoms is larger than that of the starting material olefin by one is most desirable.

When compared with the conventional methods such as a method wherein fatty acid is once formed from olefin and said fatty acid is made to react directly with alcohol in the presence of acid catalyst or a method wherein esterification is effected upon converting fatty acid into the acid chloride, the method of the present invention not only can produce the ester directly from the olefin without extracting the fatty acid but also it can separate the catalyst from said ester and directly use it repeatedly, so that the process can be drastically simplified. Besides, according to the conventional methods, in the case of a fatty acid containing branched chains, it has been difficult to manufacture an ester containing a branched chain by direct esterification of the fatty acid and an alcohol, but according to the present invention, such ester can be easily manufactured. Further, the ester obtained by separating the cobalt compound catalyst according to the present invention contains a modicum of cobalt compound dissolved therein, but this cobalt compound can be easily removed through adsorption by means of an adsorbent such as active carbon or active clay.

EXAMPLE 1

Upon placing 0.65 mole of hexene-1, 0.016 mole of cobalt octanoate, 0.24 mole of γ-picoline and 0.1 mole of water in a stainless steel autoclave having a capacity of 300 ml, 30 minutes' stirring was conducted at a temperature of 160°C while applying a pressure of 150 Kg/cm$^2$ with carbon monoxide. Next, 0.125 mole of pentaerythrito was added to the resulting mixture and 7 hours' stirring was conducted by applying the same temperature and pressure as above. When the thus reacted mixture was cooled, there was obtained a uniform liquid. After heating this reaction mixture to distill out the unreacted olefin, water and γ-picoline and then cooling the distillation residue, the cobalt compound catalyst was removed by filtration. The content of cobalt compound in the filtrate was 500 ppm in terms of cobalt metal, and the rate of recovery of cobalt was 96%.

EXAMPLE 2

The cobalt compound recovered in Example 1 was mixed with cobalt octanoate equivalent to the amount of cobalt effused into the filtrate to thereby prepare a catalyst. When this catalyst was used ten times repeatedly, the result was the same as in Example 1.

EXAMPLE 3

Upon placing 0.65 mole of decene-1, 0.016 mole of cobalt octanoate and 0.36 mole of pyridine in a stainless steel autoclave having a capacity of 300 ml, 30 minutes' stirring was conducted at a temperature of 160°C while applying a pressure of 150 Kg/cm$^2$ with carbon monoxide. Next, 0.25 mole of neopentyl glycol was added to the resulting mixture and 12 hours' stirring was conducted by applying the same temperature and pressure as above. After cooling the thus reacted mixture, carbon monoxide was removed therefrom, pyridine and unreacted olefin were distilled out by heating, the distillation residue was cooled, and the cobalt compound catalyst was removed by filtration. The content of the cobalt compound in the filtrate was 2,000 ppm in terms of cobalt metal, and the rate of recovery of cobalt was 76%.

EXAMPLE 4

Upon effecting the same reaction as in Example 3, 0.1 mole of undecane acid was added at the time of distilling out pyridine and unreacted olefin. After cooling the distillation residue, the cobalt compound catalyst was removed by filtration. The content of the cobalt compound in the filtrate was 300 ppm in terms of metal, and the rate of recovery of cobalt was 96%.

EXAMPLE 5

Upon placing 1.4 mole of butene-1, 0.008 mole of dicobalt octacarbonyl, 0.24 mole of γ-picoline, 0.1 mole of water and 100 g of tetrahydrofuran in a stainless steel autoclave having a capacity of 300 m, 10 minutes' stirring was conducted at a temperature of 160°C while applying a pressure of 150 Kg/cm$^2$ with carbon monoxide. Next, 0.125 mole of pentaerythritol was added to the resulting mixture and 6.5 hours' stirring was conducted by applying the same temperature and pressure as above. After cooling the thus reacted mixture, carbon monoxide and butene were removed therefrom, and water and picoline were distilled out by heating. After cooling the distillation residue, the cobalt compound catalyst was removed by filtration. The content of the cobalt compound in the filtrate was 300 ml in terms of metal, and the rate of recovery of cobalt was 96%.

EXAMPLE 6

Upon placing 0.65 mole of an octene mixture, 0.016 mole of cobalt octanoate, 0.24 mole of γ-picoline and 0.1 mole of water in a stainless steel autoclave having a capacity of 300 ml, 10 minutes' stirring was conducted at a temperature of 160°C while applying a pressure of 150 Kg/cm² with carbon monoxide. Next, 0.167 mole of trimethylol propane to the resulting mixture and 2 hours' stirring was conducted by applying the same temperature and pressure as above. After cooling the thus reacted mixture, carbon monoxide was removed therefrom, and then the unreacted olefin, water and picoline were distilled out by heating. After cooling, the distillation residue was subjected to 1 hour's centrifugal separation process at 3,000 G. The content of the cobalt compound in the supernatant liquid was 800 ppm, and the rate of recovery of cobalt was 84%.

What is claimed is:

1. In a method of preparing liquid polyol esters of carboxylic acids which comprises reacting an olefin having 3 to 20 carbon atoms, with carbon monoxide and polyhydric alcohol, in the presence of a cobalt catalyst, to obtain a reaction product mixture comprising the liquid polyol ester product, unreacted olefin and cobalt catalyst, the improvement which comprises: distilling the reaction product mixture under conditions effective to retain a mixture consisting essentially of the liquid polyol ester product and the cobalt catalyst as the distillation residue, cooling the distillation residue to transform the cobalt catalyst into a solid or paste-like form, and then filtering or centrifuging the distillation residue to separate the solid or paste-like cobalt catalyst from the liquid polyol ester product.

2. A method according to claim 1, wherein said olefin is employed in stoichiometric excess relative to said polyhydric alcohol.

3. A method according to claim 1, wherein said olefin having 3 to 20 carbon atoms is an olefin selected from the group consisting of propylene, butene-1, hexene-1, 2-ethyl hexene-1, octene-1, hexene-2, octene-2, tetradecene-3 and analogs thereof.

4. A method according to claim 1, wherein said polyhydric alcohol is an alcohol selected from the group consisting of ethylene glycol, trimethylol propane, pentaerythritol and analogs thereof.

5. A method according to claim 1, wherein said carbon monoxide contains less than 10% by volume of hydrogen as impurity.

6. A method according to claim 1, wherein said cobalt compound consists of at least one member selected from the group consisting of dicobalt octacarbonyl, cobalt carbonyl hydride or a compound forming these substances.

7. A method according to claim 1, wherein the reaction is effected in the presence of pyridine base and wherein said pyridine base is removed as the overhead in the step of distilling the reaction product mixture.

8. A method according to claim 7, wherein the temperature for the reaction is in the range of from 90° to 250°C and the pressure for the reaction is in the range of from 5 to 300 Kg/cm².

9. A method according to claim 8, wherein the reaction product mixture is distilled by heating in the presence of a carboxylic acid.

10. A method according to claim 8, wherein the reaction is effected in the presence of water and wherein the water is removed as the overhead in the step of distilling the reaction product mixture.

11. A method according to claim 8, wherein the amount of the catalyst is in the range of from 0.001 to 0.1 mole per 1 equivalent of the hydroxyl groups of the polyhydric alcohol in terms of cobalt metal.

12. A method according to claim 7, wherein said pyridine base is a base selected from the group consisting of pyridine, $\beta$-picoline, $\gamma$-picoline, 3.5-lutidine, 4-ethyl pyridine and analogs thereof.

13. A method according to claim 8, wherein the amount of said pyridine base is in the range of from 1 to 100 moles relative to 1 mole of catalyst metal.

14. A method according to claim 9, wherein said carboxylic acid is a fatty acid having 2 to 21 carbon atoms or an aromatic carboxylic acid having 7 to 9 carbon atoms.

* * * * *